United States Patent [19]
Dobashi et al.

[11] Patent Number: 5,175,275
[45] Date of Patent: Dec. 29, 1992

[54] METHOD FOR PREPARING POWDERY CRYSTALLINE CELLULOSE

[75] Inventors: Shozaburo Dobashi; Hisaichiro Uchida, both of Mihara; Keiso Ohara, Omiya, all of Japan

[73] Assignee: Tosco Co., Ltd., Tokyo, Japan

[21] Appl. No.: 793,001

[22] Filed: Nov. 15, 1991

Related U.S. Application Data

[63] Continuation of Ser. No. 416,491, Oct. 3, 1989, abandoned.

[51] Int. Cl.$^5$ .................... C08B 30/00; C13F 3/00; A01N 25/00
[52] U.S. Cl. ..................... 536/56; 536/124; 127/29; 127/34; 514/781; 435/99; 435/277
[58] Field of Search ............... 536/56, 124; 127/29, 127/34; 514/781; 435/99, 277

[56] References Cited

U.S. PATENT DOCUMENTS

| | | | |
|---|---|---|---|
| 3,972,775 | 8/1976 | Wilke et al. | 435/813 |
| 3,984,339 | 10/1976 | Takeo et al. | 536/56 |
| 4,266,981 | 5/1981 | Tsao et al. | 435/99 |
| 4,281,063 | 7/1981 | Tsao et al. | 536/56 |
| 4,427,778 | 1/1984 | Zabriskie | 435/277 |
| 4,958,014 | 9/1990 | Shirokaze | 536/56 |

Primary Examiner—Nathan M. Nutter
Attorney, Agent, or Firm—Seed and Berry

[57] ABSTRACT

The present invention relates to powdery crystalline cellulose having an average particle size ranging from 3 to 30 μm and an average degree of polymerization ranging from 400 to 1,500. The powdery crystalline cellulose can be prepared according to a method comprising treating a starting cellulose material with a cellulase, subjecting the enzyme-treated cellulose material to acid hydrolysis under mild conditions, and then mechanically pulverizing the hydrolyzed cellulose material. The powdery crystalline cellulose is suitable for various applications of foods, cosmetics, medicines and various industrial products.

13 Claims, No Drawings

METHOD FOR PREPARING POWDERY CRYSTALLINE CELLULOSE

CROSS-REFERENCE TO RELATED APPLICATIONS

This application is a continuation application of U.S. Ser. No. 07/416,491, filed Oct. 3, 1989, now abandoned.

BACKGROUND OF THE INVENTION

1. Field of the Invention

The present invention relates to powdery crystalline cellulose and a method for preparing the same and more specifically to novel powdery crystalline cellulose having a specific average degree of polymerization and a specific average particle size, and a method for preparing the same.

2. Description of the Prior Art

Recently, foods, cosmetics, medicines as well as various industrial products have been diversified in their applications and they have been required to have high qualities in order to meet the requirements of such application. Therefore, there is big demand that powdery crystalline cellulose to be used in such applications must have a high purity, a high degree of polymerization and a fine particle size.

Up to now, the powdery crystalline cellulose has been conventionally obtained by hydrolyzing, with an acid, a natural cellulose material such as cotton, flax, ramie, jute or hemp, paper or wood; a regenerated cellulose material such as rayon or cuprammonium rayon; or a processed product thereof, to remove its non-crystalline part and then mechanically pulverizing the resultant product, as disclosed in Japanese Patent Publication for Opposition Purpose (hereinafter referred to as "J. P. KOKOKU") No. 40-26274.

It is known that cellulose is decomposed by a cellulose derived from mold, bacteria or the like as described in IWANAMI RIKAGAKU JITEN (IWANAMI Physicochemical Dictionary), 3rd ed., 736, issued by IWANAMI BOOK COMPANY.

In such conventional methods for preparing powdery crystalline cellulose, the fiber strength of the cellulose materials should be lowered to facilitate the mechanical pulverization of the cellulose material and to obtain fine powdery crystalline cellulose with a high purity. For this reason, strict conditions are necessary for the hydrolysis with an acid. For instance, the hydrolysis with an acid is carried out at 100° C. for several hours at an acid concentration of 1N when hydrochloric acid is used and at 50° C. for several hours to ten and several hours at an acid concentration of 5N when sulfuric acid is used.

However, the degree of polymerization of the cellulose fibers per se is greatly lowered under such severe hydrolysis conditions and, therefore, it is impossible to obtain physically and chemically stable fine powdery crystalline cellulose having excellent mechanical strength and durability. Therefore, a method for preparing powdery crystalline cellulose having a high degree of polymerization has been strongly demanded to be developed.

SUMMARY OF THE INVENTION

Accordingly, an object of the present invention is to provide powdery crystalline cellulose having a degree of polymerization higher than that of the conventional powdery crystalline cellulose.

Another object of the present invention is to provide powdery crystalline cellulose having a specific average degree of polymerization and a specific average particle size.

A further object of the present invention is to provide a method for preparing such powdery crystalline cellulose.

The inventors of this invention have conducted various and intensive studies to achieve the foregoing objects and, as a result, have found out that powdery crystalline cellulose having a fine particle size, a high degree of polymerization and a high purity can be obtained by combining a mild acid hydrolysis with a treatment with a cellulase. The present invention has been completed based on this finding.

According to an aspect of the present invention, there is provided powdery crystalline cellulose having an average particle size of 3 to 30 $\mu$m and an average degree of polymerization of 400 to 1,500.

According to another aspect of the present invention, there is provided a method for preparing powdery crystalline cellulose which comprises the steps of treating a cellulose material with a cellulase, then subjecting the enzyme-treated cellulose material to an acid hydrolysis under mild conditions and mechanically pulverizing the hydrolyzed cellulose material.

DETAILED EXPLANATION OF THE INVENTION

The powdery crystalline cellulose of the present invention can be obtained by a combination of a mild acid hydrolysis with a treatment with a cellulase. The inventors of the present invention have discovered such a combination as an effective tool for preparing findings.

First of all, to increase the degree of polymerization of cellulose, it is necessary to use a cellulose material having a high degree of polymerization as a starting material. Such an idea has been conventionally known. However, to obtain fine powder having an average particle size as low as not more than 10 $\mu$m, it is required to control the strength of a cellulose material prior to mechanical pulverization to an extremely low level, for instance, not more than 0.5 g per denier expressed in terms of a fiber strength. If it exceeds 1 g per denier, good pulverization cannot be expected. Moreover, if the acid hydrolysis is performed so that the fiber strength is lowered, the degree of polymerization of the starting cellulose material is also reduced. For instance, the degree is reduced to not more than 400 even if a cellulose having a degree of polymerization of about 5,000 is used. Therefore, powdery crystalline cellulose having a high degree of polymerization cannot be produced by such a method.

The inventors of this invention have investigated, under such circumstances, a method for reducing the mechanical strength of cellulose while maintaining the degree of polymerization of the cellulose as high as possible. As a result, the inventors have found out that such a purpose can be attained by making use of a cellulase, an enzyme decomposing cellulose. More specifically, the cellulase restricts the reduction in the degree of polymerization of cellulose to a very low level although it greatly decreases the mechanical strength of cellulose as compared with the acid hydrolysis. For instance, the mechanical strength of the cellulose is reduced to 60 to 90% of the original value through a cellulase treatment, but the degree of polymerization thereof is reduced to a level as low as 10 to 40%. If a cellulose material treated with the enzyme is further hydrolyzed with an acid under mild conditions, the mechanical strength and degree of polymerization are naturally reduced, but the extent of the reduction in the degree of polymerization is quite low as compared with those processed according to the conventional methods. For this reason, the acid-hydrolyzed cellulose material can be mechanically pulverized very smoothly to easily obtain highly pure and fine powdery crystalline cellulose while maintaining its high degree of polymerization.

The present invention will hereinafter be explained in more detail.

The cellulose materials usable in the present invention may be any materials conventionally used as starting materials for preparing powdery crystalline cellulose. Specific examples thereof include natural cellulose materials such as ramie, cotton, flax, jute or hemp, paper and wood pulp; regenerated cellulose materials such as rayon, cellophane and cuprammonium rayon; and processed materials such as bleached sulfite pulp and bleached sulfate pulp.

Any kind of cellulase can be used so long as it can cleave the $\beta$-1,4-glycoside bond of cellulose through hydrolysis. The sources of the cellulase are not limited and include those cellulases derived from mold, bacteria, protozoon, plants such as germinating seeds, and animals such as snails.

According to the present invention, the starting cellulose material is first treated with the aforesaid cellulose. In general, the kinds and the amount of the cellulases slightly vary depending on the properties of the starting cellulose material, but the concentration of the cellulase preferably ranges from 20 to 60 U/g. The enzyme treatment is preferably performed at a pH value ranging from 5.0 to 6.5, at a temperature ranging from 30° to 50° C. for 2 to 3 hours.

The cellulase is generally used in the form of solution or suspension in water or an organic solvent. The cellulase may also be used in the form of a paste. Water is preferably used as a medium for the cellulase from the viewpoint of safety, economics and handling properties.

In addition, chemicals such as nonionic, anionic or cationic surfactants and pH stabilizing agents, for instance, a combination of acetic acid with sodium acetate or hydrochloric acid with sodium citrate may also be simultaneously used unless they exert adverse influences on the activity of the cellulase.

The enzyme treated cellulose thus obtained is preferably washed with water sufficiently.

Then, the enzyme treated cellulose is subjected to acid hydrolysis utilizing a mineral acid. Examples of mineral acids include hydrochloric acid and sulfuric acid. Any acid hydrolysis conditions can be used so long as the mineral acid acts on the non-crystalline part of the cellulose. For instance, the acid hydrolysis can be performed at a mineral acid concentration ranging from 0.1 to 8.0N, a temperature ranging from 40° to 125° C. for 5 minutes to 9 hours. When hydrochloric acid is used, the hydrolysis is carried out at a acid concentration of 0.1 to 2.5N, a temperature of 60° to 125° C. for 5 to 120 minutes. When sulfuric acid is used, the hydrolysis is performed at a acid concentration of 0.2 to 8.0N, a temperature of 40° to 120° C. for 0.5 to 9 hours.

Then, the acid hydrolyzed cellulose is mechanically pulverized. Apparatuses for pulverization usable herein may be any type conventionally used in such a pulverization processing such as pulverizers and mills. The pulverization time is, for instance, in the range of from 1 to 10 hours and preferably 2 to 7 hours.

At this stage, the cellulose powder thus obtained may optionally be sieved to remove coarse cellulose particles and control the particle size. Sieves of 42 to 200 mesh are commonly used in the present invention.

As already explained above, the starting cellulose material is treated with the cellulase prior to the acid hydrolysis and mechanical pulverization in the present method. Therefore, the strength of the cellulose fibers can be reduced while suppressing the reduction in the degree of polymerization to a level as low as possible. This is probably because the cellulase attacks interstices of fibrils along spiral planes of cellulose fiber crystals to make cracks along the axis of the cellulose fibers. If the enzyme treated cellulose is then subjected to a mild acid hydrolysis, the strength of the cellulose fibers can further be lowered to the extent that they can be formed into fine particles, while maintaining the degree of polymerization as high as possible. When the acid treated cellulose is subsequently mechanically pulverized, there can be obtained highly pure powdery crystalline cellulose having a high degree of polymerization and a fine particle size. If the cellulose is hydrolyzed under severe acid hydrolysis conditions to reduce the strength of the cellulose fibers, fine crystalline cellulose particles can be obtained without treating the cellulose with an enzyme, but the degree of polymerization of the cellulose powder after the pulverization is reduced to not more than 400. Moreover, if the cellulose is mechanically pulverized immediately after the enzyme treatment, a large amount of the cellulose has still its fibrous form and thus fine powdery crystalline cellulose cannot be obtained.

The present invention will hereunder be explained in more detail with reference to the following non-limitative working Examples and the effects practically achieved by the present invention will also be discussed in detail in comparison with Comparative Examples. Examples 1 to 6 and Comparative Examples 1 to 4.

Bast fiber having an average degree of polymerization of 4,000 and the fiber strength of 6.5 g/denier was treated with an aqueous solution of a cellulose commercially available from NOVO CO., LTD. under the trade name of CELLUCRAST at an enzyme concentration of 50 U/g, a temperature of 35° C., a pH value of 5.0 for 3 hours to obtain cellulose fibers having an average degree of polymerization of 2,800 and the fiber strength of 0.6 g/denier. Then, the enzyme-treated cellulose was subjected to an acid hydrolysis using various mineral acids listed in the following Table I, under the conditions (such as mineral acid concentrations, hydrolysis temperature and time) summarized in Table I, followed by washing the hydrolyzed cellulose fibers with water, drying them, then introducing them into a pulverizer manufactured and sold by HOSOKAWA MICRON CO., LTD., pulverizing the same in FINE VIBRATION MILL manufactured and sold by CHUOKAKOKI CO., LTD., subsequently passing the pulverized fibers through a sieve of 42 mesh to remove coarse particles, and then determining the average degree of polymerization and the average particle size of the resulting powdery crystalline cellulose. The results obtained are listed in Table I.

On the other hand, the same bast fiber was treated according to the same procedures as those explained above except that it was not subjected to the enzyme treatment, to obtain comparative powdery crystalline cellulose samples. The average degree of polymerization and the average particle size of these comparative samples were likewise determined and listed in Table I.

TABLE I

| Ex. No. | Acid | Conc. (N) | T (°C.) | t (min) | A.D.P. | A.P.S. (μm) |
|---|---|---|---|---|---|---|
| 1 | HCl | 0.1 | 60 | 20 | 1,480 | 29 |
| 2 | HCl | 0.1 | 60 | 30 | 1,030 | 21 |
| 3 | HCl | 0.2 | 60 | 30 | 720 | 12 |
| 4 | HCl | 0.3 | 60 | 30 | 410 | 4 |
| 5 | $H_2SO_4$ | 2.5 | 60 | 120 | 1,360 | 25 |
| 6 | $H_2SO_4$ | 2.5 | 60 | 90 | 830 | 16 |
| 1* | HCl | 1.0 | 110 | 120 | 80 | 15 |
| 2* | HCl | 1.0 | 90 | 60 | 450 | A |
| 3* | $H_2SO_4$ | 4.65 | 60 | 480 | 80 | 13 |
| 4* | $H_2SO_4$ | 4.65 | 60 | 240 | 750 | A |

A.D.P.: Average degree of polymerization.
A.P.S.: Average particle size.
*: Comparative Example
A: Fibrous cellulose remains in the product.

As seen from the results listed in Table I, the powdery crystalline cellulose obtained according to the present invention has a high average degree of polymerization, a low average particle size and a high purity as compared with the products obtained in Comparative Examples.

What is claimed is:

1. A method for preparing powdery crystalline cellulose having an average particle size ranging from 3 to 30 μm and an average degree of polymerization ranging from 400 to 1,500, comprising the steps of:
   treating a starting cellulose material with a cellulase;
   subjecting the cellulase-treated cellulose material to acid hydrolysis under mild conditions to yield a hydrolyzed cellulose material; and
   mechanically pulverizing the hydrolyzed cellulose material to yield the powdery crystalline cellulose.

2. The method of claim 1, wherein the cellulase has a concentration ranging from 20 to 60 U/g.

3. The method of claim 1, wherein the cellulase is used in the form of an aqueous solution.

4. The method of claim 1, wherein the cellulase-treatment is performed at a pH value ranging from 5.0 to 6.5 and at a temperature ranging from 30° C. to 50° C. for 2 to 3 hours.

5. The method of claim 1, wherein the cellulase-treatment is carried out in the presence of a surfactant, a pH stabilizing agent, or both.

6. The method of claim 1, wherein the acid hydrolysis is performed at a mineral acid concentration ranging from 0.1 to 8.0N and a temperature ranging from 40° C. to 125° C. for 5 minutes to 9 hours.

7. The method of claim 6, wherein the mineral acid is hydrochloric acid and the acid hydrolysis is carried out at an acid concentration ranging from 0.1 to 2.5N and a temperature ranging from 60° C. to 125° C. for 5 to 120 minutes.

8. The method of claim 6, wherein the mineral acid is sulfuric acid and the acid hydrolysis is carried out at an acid concentration ranging from 0.2 to 8.0N and a temperature ranging from 40° C. to 120° C. for 30 minutes to 9 hours.

9. The method of claim 1, wherein the pulverization is conducted for 1 to 10 hours.

10. The method of claim 1, wherein the pulverization is conducted for 2 to 7 hours.

11. The method of claim 1, wherein the powdery crystalline cellulose is further sieved to control the particle size of the powdery crystalline cellulose.

12. The method of claim 11, wherein the size of the sieve ranges from 42 to 200 mesh.

13. A method for preparing powdery crystalline cellulose having an average particle size ranging from 3 to 30 μm and an average degree of polymerization ranging from 400 to 1,500, comprising the steps of:
   treating a starting cellulose material with a cellulase at a pH value ranging from 5.0 to 6.5 and at a temperature ranging from 30° C. to 50° C. for 2 to 3 hours;
   subjecting the cellulase-treated cellulose material to acid hydrolysis at a mineral acid concentration ranging from 0.1 to 8.0N and a temperature ranging from 40° C. to 125° C. for 5 minutes to 9 hours to yield a hydrolyzed cellulose material; and
   mechanically pulverizing the hydrolyzed cellulose material to yield the powdery crystalline cellulose.

* * * * *